US010544464B2

(12) United States Patent
Xing

(10) Patent No.: US 10,544,464 B2
(45) Date of Patent: Jan. 28, 2020

(54) TERT PROMOTER MUTATIONS IN CANCER

(71) Applicant: THE JOHNS HOPKINS UNIVERSITY, Baltimore, MD (US)

(72) Inventor: Michael Mingzhao Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 605 days.

(21) Appl. No.: 14/780,600

(22) PCT Filed: Mar. 27, 2014

(86) PCT No.: PCT/US2014/031967
§ 371 (c)(1),
(2) Date: Sep. 28, 2015

(87) PCT Pub. No.: WO2014/160834
PCT Pub. Date: Oct. 2, 2014

(65) Prior Publication Data
US 2016/0040250 A1 Feb. 11, 2016

Related U.S. Application Data

(60) Provisional application No. 61/833,773, filed on Jun. 11, 2013, provisional application No. 61/805,710, filed on Mar. 27, 2013.

(51) Int. Cl.
C12Q 1/68 (2018.01)
C12Q 1/6886 (2018.01)

(52) U.S. Cl.
CPC ..... *C12Q 1/6886* (2013.01); *C12Q 2600/106* (2013.01); *C12Q 2600/112* (2013.01); *C12Q 2600/156* (2013.01)

(58) Field of Classification Search
None
See application file for complete search history.

(56) References Cited

PUBLICATIONS

Horikawa et al; Cancer Research, vol. 59, pp. 826-830; 1999.*
Devereux, T., et al., "Methylation analysis of the promoter region of the human telomerase reverse transcriptase (hTERT) gene", Cancer Research, Dec. 15, 1999, vol. 59, pp. 6087-6090.
Gu, J., et al., "Telomerase promoter-driven cancer gene therapy", Cancer Biology & Therapy, vol. 2, No. 4, Suppl. 1, S64-S70; Jul./Aug. 2003.
Horn, S., et al., "TERT promoter mutations in familial and sporadic melanoma", Science, Feb. 22, 2013, vol. 339, pp. 959-961.
Liu, T., et al., "The age-and shorter telomere-dependent TERT promoter mutation in follicular thyroid cell-derived carcinomas", Oncogene, (2013) pp. 1-7.
Poole, J., et al., Activity, function, and gene regulation of the catalytic subunit of telomerase (hTERT), Gene 269, (2001), pp. 1-12.
Takeda, T., et al., "Tumor-specific gene therapy for undifferentiated thyroid carcinoma utilizing the telomerase reverse transcriptase promoter", The Journal of Clinical Endocrinology & Metabolism, (2003), vol. 88, No. 3, pp. 3531-3538.
Capezzone, M., et al., "Telomeres and thyroid cancer" Current Genomics (2009) 10 526-533.
Davies, H., et al., Mutations of the BRAF gene in human cancer. Nature (2002) 417 949-954.
Rochakonda, P., et al., TERT promoter mutations in bladder cancer affect patient survival and disease recurrence through modification by a common polymorphism, PNAS (2013) vol. 110, No. 43, pp. 17426-17431.
Horn, S., et al. TERT promoter mutations in familial and sporadic melanoma. Science (2013) 339 959-961.
Hurst, et al., Comprehensive Mutation Analysis of the TERT Promoter in Bladder Cancer and Detection of Mutations in Voided Urine, European Urology 65 (2014) 367-369.
Hu, S, et al. Association of aberrant methylation of tumor suppressor genes with tumor aggressiveness and BRAF mutation in papillary thyroid cancer. International Journal of Cancer (2006) 119 2322-2329.
Huang, F., et al., Highly recurrent TERT promoter mutations in human melanoma. Science (2013) 339 957-959.
Janknect, R., et al., SAP1a is a nuclear target of signaling cascades involving ERKs. Oncogene (1995) 10 1209-1216.
Jemal A., et al., Global cancer statistics. CA: A Cancer Journal for Clinicians (2011) 61 69-90.
Killela, P., et al., TERT promoter mutations occur frequently in gliomas and a subset of tumors derived from cells with low rates of self-renewal. PNAS (2013) 110 6021-6026.
Liu, X., et al., Highly prevalent TERT promoter mutations in bladder cancer and glioblastoma. Cell Cycle (2013) 12 1637-1638.
Livolsi, V., Papillary carcinoma tall cell variant (TCV): a review. Endocrine Pathology (2010) 21 12-15.
Mocellin, S., et al., Telomerase and the search for the end of cancer. Trends in Molecular Medicine (2013) 19 125-133.

(Continued)

Primary Examiner — Jehanne S Sitton
(74) Attorney, Agent, or Firm — Johns Hopkins Technology Ventures

(57) ABSTRACT

The present invention relates to the field of cancer. More specifically, the present invention provides methods and compositions related to certain promoter mutations in cancer. In one embodiment, a method for treating a subject having thyroid cancer comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; (c) identifying the subject as having or likely to develop aggressive thyroid cancer if the C228T and/or C250T mutation is identified; and (d) treating the subject with one or more treatment modalities appropriate for a subject having or likely to develop aggressive thyroid cancer.

6 Claims, 3 Drawing Sheets
Specification includes a Sequence Listing.

(56) References Cited

PUBLICATIONS

Smallridge, R., et al., American Thyroid Association Anaplastic Thyroid Cancer Guidelines Taskforce. American Thyroid Association guidelines for management of patients with anaplastic thyroid cancer. Thyroid (2012) 22 1104-1139.

Smekalova, E., et al., Telomerase RNA biosynthesis and processing. Biochemistry (2012) 77 1120-1128.

Van Staveren, W., et al., Human thyroid tumor cell lines derived from different tumor types present a common dedifferentiated phenotype. Cancer Research (2007) 67 8113-8120.

Strahl, T., et al., Selective response of ternary complex factor Sap1a to different mitogen-activated protein kinase subgroups. PNAS (1996) 93 11563-11568.

Whitmarsh, A., et al., Integration of MAP kinase signal transduction pathways at the serum response element. Science (1995) 269 403-407.

Xing, M., et al., BRAF mutation in thyroid cancer. Endocrine-Related Cancer (2005) 12 245-262.

Xing, M., et al., The T1799A BRAF mutation is not a germline mutation in familial nonmedullary thyroid cancer. Clinical Endocrinology (2005) 63 263-266. 2005b.

Xing, M., et al., Molecular pathogenesis and mechanisms of thyroid cancer. Nature Reviews. Cancer (2013) 13 184-199.

Xing, M., et al., BRAF mutation predicts a poorer clinical prognosis for papillary thyroid cancer. Journal of Clinical Endocrinology and Metabolism (2005) 90 6373-6379.

Xing, M. et al., Association between BRAF V600E mutation and mortality in patients with papillary thyroid cancer. Journal of the American Medical Association (2013) 309 1493-1501.

Xing, M., et al., Promises in molecular-based management of differentiated thyroid cancer. Lancet (2013) 381 1058-1069.

Ghossein, R., et al., Tall cell variant of papillary thyroid carcinoma without extrathyroid extension: biologic behavior and clinical implications. Thyroid (2007) vol. 17 No. 7.

\* cited by examiner

SEQUENCE LISTING

<160> NUMBER OF SEQ ID NOS: 7

<210> SEQ ID NO 1
<211> LENGTH: 11
<212> TYPE: DNA
<213> ORGANISM: Homo sapiens

<400> SEQUENCE: 1
ccccttccgg g                                                      11

<210> SEQ ID NO 2
<211> LENGTH: 20
<212> TYPE: DNA
<213> ORGANISM: Artificial Sequence
<220> FEATURE:
<223> OTHER INFORMATION: TERT promoter sense primer

<400> SEQUENCE: 2
agtggattcg cgggcacaga                                             20

<210> SEQ ID NO 3
<211> LENGTH: 18
<212> TYPE: DNA
<213> ORGANISM: Artificial Sequence
<220> FEATURE:
<223> OTHER INFORMATION: TERT promoter antisense primer

<400> SEQUENCE: 3
cagcgctgcc tgaaactc                                               18

<210> SEQ ID NO 4
<211> LENGTH: 23
<212> TYPE: DNA
<213> ORGANISM: Artificial Sequence
<220> FEATURE:
<223> OTHER INFORMATION: BRAF V600E sense primer

<400> SEQUENCE: 4

```
tcataatgct tgctctgata gga                                                    23

<210> SEQ ID NO 5
<211> LENGTH: 22
<212> TYPE: DNA
<213> ORGANISM: Artificial Sequence
<220> FEATURE:
<223> OTHER INFORMATION: BRAF V600E antisense primer

<400> SEQUENCE: 5
ggccaaaaat ttaatcagtg ga                                                     22

<210> SEQ ID NO 6
<211> LENGTH: 32
<212> TYPE: DNA
<213> ORGANISM: Artificial Sequence
<220> FEATURE:
<223> OTHER INFORMATION: Human TERT sense strand

<400> SEQUENCE: 6
cccctcccgg gtccccggcc cagccccctc cg                                          32

<210> SEQ ID NO 7
<211> LENGTH: 32
<212> TYPE: DNA
<213> ORGANISM: Artificial Sequence
<220> FEATURE:
<223> OTHER INFORMATION: Human TERT antisense strand

<400> SEQUENCE: 7 cggaggggc tgggccgggg acccgggagg gg                                           32
```

TERT PROMOTER MUTATIONS IN CANCER

CROSS-REFERENCE TO RELATED APPLICATIONS

This application is a 35 U.S.C. § 371 U.S. national entry of International Application PCT/US2014/031967, having an international filing date of Mar. 27, 2014, which claims the benefit of U.S. Provisional Application No. 61/805,710, filed Mar. 27, 2013, and U.S. Provisional Application No. 61/833,773, filed Jun. 11, 2013, the content of each of the aforementioned applications is herein incorporated by reference in their entirety.

STATEMENT OF GOVERNMENTAL INTEREST

This invention was made with government support under grant no. RO1CA134225, awarded by the National Institutes of Health. The government has certain rights in the invention.

FIELD OF THE INVENTION

The present invention relates to the field of cancer. More specifically, the present invention provides methods and compositions related to certain promoter mutations in cancer.

INCORPORATION-BY-REFERENCE OF MATERIAL SUBMITTED ELECTRONICALLY

This application contains a sequence listing. It has been submitted electronically via EFS-Web as an ASCII text file entitled "P12422-03_ST25.txt." The sequence listing is 1,605 bytes in size, and was created on Mar. 27, 2014. It is hereby incorporated by reference in its entirety.

BACKGROUND OF THE INVENTION

Thyroid cancer is the most common classical endocrine malignancy, and its incidence has been rising rapidly in the US as well as other industrialized countries over the past few decades. Thyroid cancers are classified histologically into four groups: papillary, follicular, medullary, and undifferentiated or anaplastic thyroid carcinomas. If diagnosed at an early stage, thyroid cancer is a well manageable disease with a 5-year survival rate of 97% among all patients. Survival rate is poorer (about 40%) among individuals that are diagnosed with a more advanced disease; i.e., individuals with large, invasive tumors and/or distant metastases have a 5-year survival rate of about 40%. For radioiodine-resistant metastatic disease, there is no effective treatment and the 10-year survival rate among these patients is less than 15%.

Although relatively rare (1% of all malignancies in the US), the incidence of thyroid cancer more than doubled between 1984 and 2004 in the US. Between 1995 and 2004, thyroid cancer was the third fastest growing cancer diagnosis, behind only peritoneum, omentum, and mesentery cancers and "other" digestive cancers. Similarly, dramatic increases in thyroid cancer incidence have also been observed in Canada, Australia, Israel, and several European countries. Thus, there is a need for better understanding of the molecular causes of thyroid cancer progression to develop new diagnostic tools and better treatment options.

SUMMARY OF THE INVENTION

The present invention is based, at least in part, on the discovery that certain mutations in the promoter region of the telomerase reverse transcriptase (TERT) gene are prevalent in certain cancer—thyroid, bladder and glioblastoma, thus representing new diagnostic, prognostic and therapeutic targets.

More specifically, we explored mutations 1 295 228 C>T and 1 295 250 C>T (termed C228T and C250T respectively), corresponding to −124 C>T and −146 C>T from the translation start site in the promoter of the telomerase reverse transcriptase (TERT) gene, in thyroid cancers by genomic sequencing of a large number of primary tumor samples. We found the C228T mutation in 0 of 85 (0.0%) benign thyroid tumors, 30 of 257 (11.7%) papillary thyroid cancers (PTC), 9 of 79 (11.4%) follicular thyroid cancers (FTC), 3 of 8 (37.5%) poorly differentiated thyroid cancers (PDTC), 23 of 54 (42.6%) anaplastic thyroid cancers (ATC), and 8 of 12 (66.7%) thyroid cancer cell lines. The C250T mutation was uncommon, but mutually exclusive with the C228T mutation, and the two mutations were collectively found in 11 of 79 (13.9%) FTC, 25 of 54 (46.3%) ATC, and 11 of 12 (91.7%) thyroid cancer cell lines. Among PTC variants, the C228T mutation was found in 4 of 13 (30.8%) tall-cell PTC (TCPTC), 23 of 187 (12.3%) conventional PTC, and 2 of 56 (3.6%) follicular variant PTC samples. No TERT mutation was found in 16 medullary thyroid cancer samples. The C228T mutation was associated with the BRAF V600E mutation in PTC, being present in 19 of 104 (18.3%) BRAF mutation-positive PTC vs. 11 of 153 (7.2%) the BRAF mutation-negative PTC samples (P≤0.0094). Conversely, BRAF mutation was found in 19 of 30 (63.3%) C228T mutation-positive PTC vs. 85 of 227 (37.4%) C228T mutation-negative PTC samples (P≤0.0094). Thus, for the first time, to our knowledge, we demonstrate TERT promoter mutations in thyroid cancers that are particularly prevalent in the aggressive thyroid cancers TCPTC, PDTC, ATC and BRAF mutation-positive PTC, revealing a novel genetic background for thyroid cancers. In addition, as further described herein, we found highly prevalent TERT promoter mutations in bladder cancer and glioblastoma.

Accordingly, in one aspect, the present invention provides methods of treatment of subject having thyroid cancer. In one embodiment, a method for treating a subject having thyroid cancer comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; (c) identifying the subject as having or likely to develop aggressive thyroid cancer if the C228T and/or C250T mutation is identified; and (d) treating the subject with one or more treatment modalities appropriate for a subject having or likely to develop aggressive thyroid cancer. In a specific embodiment, the assay of step (b) comprises sequencing of the TERT promoter region comprising −124 and −146 from the translation start site in the promoter of TERT.

In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3.

In particular embodiments, the treatment modality for aggressive thyroid cancer comprises one or more of thyroidectomy, hemithyroidectomy, radioactive iodine therapy, and combinations thereof. In a further embodiment, the treatment modality comprises administering to the subject a TERT inhibitor.

In another aspect, the present invention provides methods of identifying a subject as having or likely to develop aggressive thyroid cancer, and treatment thereof. In one embodiment, a method for identifying a subject as having or likely to develop aggressive thyroid cancer comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; and (c) identifying the subject as having or likely to develop aggressive thyroid cancer if the C228T and/or C250T mutation is identified. In a specific embodiment, the assay of step (b) comprises sequencing of the TERT promoter region comprising −124 and −146 from the translation start site in the promoter of TERT.

In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3.

In certain embodiments, the method further comprises the step of administering a treatment modality appropriate for a subject having or likely to develop aggressive thyroid cancer. In particular embodiments, the treatment modality for aggressive thyroid cancer comprises thyroidectomy, hemithyroidectomy, radioactive iodine therapy, and combinations thereof. In a further embodiment, the treatment modality comprises administering to the subject a TERT inhibitor.

Accordingly, in another aspect, the present invention provides methods of treatment of subject having bladder cancer. In one embodiment, a method for treating a subject having bladder cancer comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; (c) identifying the subject as having or likely to develop bladder cancer if the C228T and/or C250T mutation is identified; and (d) treating the subject with one or more treatment modalities appropriate for a subject having or likely to develop bladder. In certain embodiments, the biological sample is a urine sample. In a specific embodiment, the assay of step (b) comprises sequencing of the TERT promoter region comprising −124 and −146 from the translation start site in the promoter of TERT. In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3.

In another aspect, the present invention provides methods of identifying a subject as having or likely to develop bladder cancer, and treatment thereof. In one embodiment, a method for identifying a subject as having or likely to develop bladder cancer comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; and (c) identifying the subject as having or likely to develop bladder cancer if the C228T and/or C250T mutation is identified. In a specific embodiment, the assay of step (b) comprises sequencing of the TERT promoter region comprising −124 and −146 from the translation start site in the promoter of TERT.

In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3. In particular embodiments, the biological sample is a urine sample.

In particular embodiments, the treatment modality for bladder cancer comprises one or more of surgery including, but not limited to, transurethral resection (with fulguration), radical cystectomy, partial cystectomy, and urinary diversion; radiation therapy, chemotherapy (e.g., intravesical); and biologic therapy such as BCG (bacillus Calmette Guerin). In a further embodiment, the treatment modality comprises administering to the subject a TERT inhibitor.

In a further aspect, the present invention provides methods of treatment of subject having glioblastoma. In one embodiment, a method for treating a subject having glioblastoma comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; (c) identifying the subject as having or likely to develop glioblastoma if the C228T and/or C250T mutation is identified; and (d) treating the subject with one or more treatment modalities appropriate for a subject having or likely to develop bladder. In a specific embodiment, the assay of step (b) comprises sequencing of the TERT promoter region comprising −124 and −146 from the translation start site in the promoter of TERT. In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3.

In yet another aspect, the present invention provides methods of identifying a subject as having or likely to develop glioblastoma, and treatment thereof. In one embodiment, a method for identifying a subject as having or likely to develop glioblastoma comprises the steps of (a) obtaining a biological sample from the subject; (b) performing an assay on the sample obtained from the subject to identify a mutation at 1 295 228 C>T (C228T) and 1 295 250 C>T (C250T), corresponding to −124 C>T and −146 C>T from the translation start site in the promoter of the telomerase reverse transcriptase (TERT) gene; and (c) identifying the subject as having or likely to develop glioblastoma if the C228T and/or C250T mutation is identified. In a specific embodiment, the assay of step (b) comprises sequencing of the TERT promoter region comprising −124 and −146 from the translation start site in the promoter of TERT.

In another specific embodiment, the assay of step (b) comprises the steps of (i) extracting DNA from the biological sample; (ii) contacting the DNA with a primer that specifically hybridizes to the TERT gene; (iii) amplifying by polymerase chain reaction (PCR) a region of the TERT gene that comprises −124 and −146 from the translation start site in the promoter of TERT; and (iv) sequencing the amplification product to identify the presence of the C228T and/or C250T mutation. In certain embodiments, the primer comprises SEQ ID NO:2 and/or SEQ ID NO:3. In particular embodiments, the biological sample is a urine sample.

In particular embodiments, the treatment modality for brain cancer including glioblastoma comprises one or more of surgery, radiation therapy (e.g., 3-dimensional radiation therapy, intensity-modulated radiation therapy, sterotactic radiation therapy, and proton beam radiation therapy); chemotherapy (e.g., intrathecal); and biologic therapy (e.g., tyrosine kinase inhibitor therapy, vascular endothelial growth factor (VEGF) therapy, dendritic call vaccine therapy, and gene therapy). In a further embodiment, the treatment modality comprises administering to the subject a TERT inhibitor.

BRIEF DESCRIPTION OF THE FIGURES

FIG. 1A: The sense DNA strand obtained using the sense primer for sequencing, displaying TERT promoter mutations C228T and C250T in various thyroid cancer cell lines and thyroid cancer samples. FIG. 1B: The antisense DNA strand obtained using the antisense primer for sequencing, displaying TERT promoter mutations G228A and G250A in various thyroid cancer cell lines and thyroid cancer samples. FIG. 1A and 1B: WRO cell line is used to show the wild-type human TERT promoter. PTC, papillary thyroid cancer; FTC, follicular thyroid cancer; ATC, anaplastic thyroid cancer; PDTC, poorly differentiated thyroid cancer.

DETAILED DESCRIPTION OF THE INVENTION

Figure 1A:
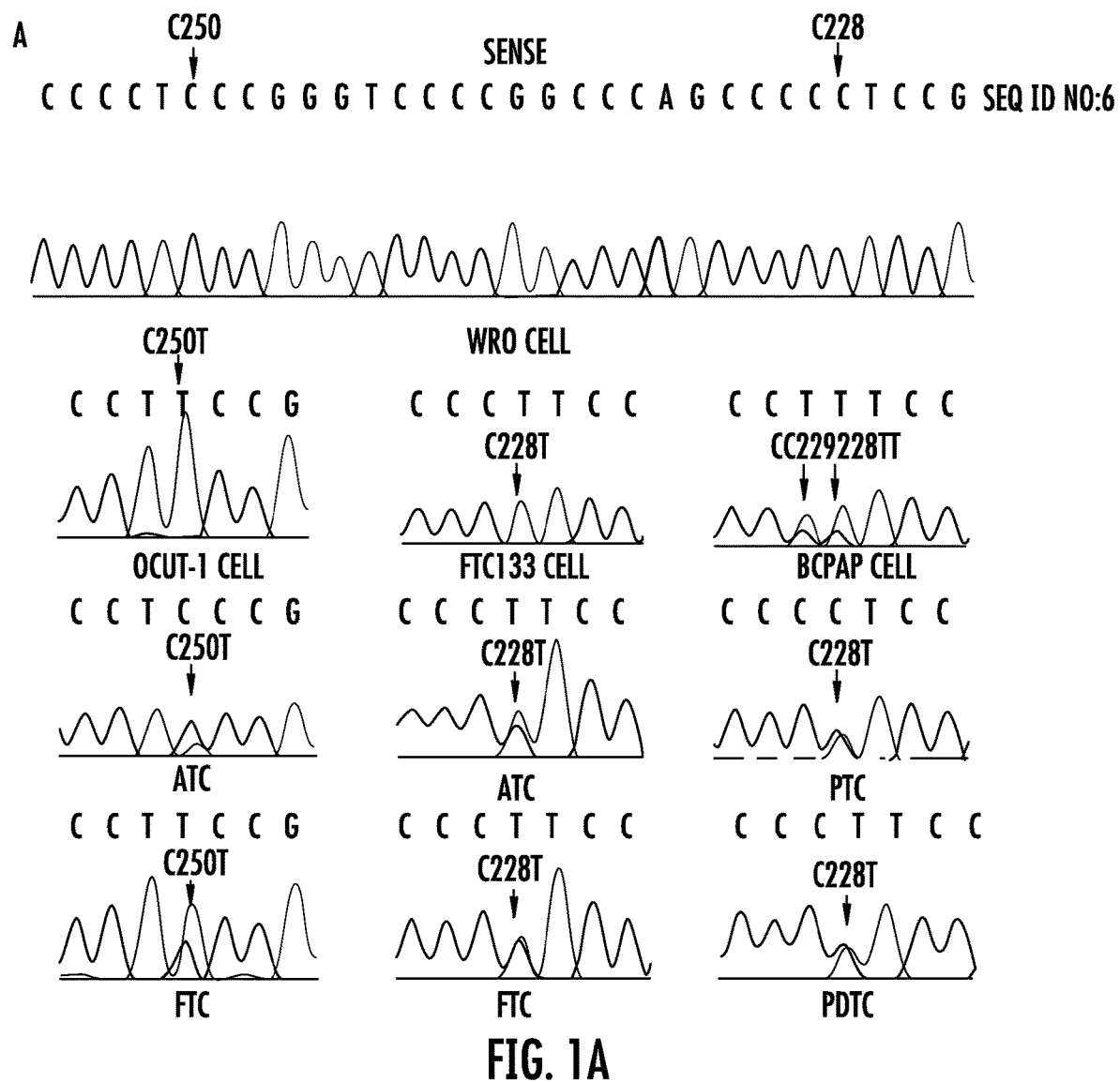
FIG. 1A-1B. Sequencing of the human TERT promoter electropherograms. Representative electropherograms of the genomic DAN sequencing of the human TERT promoter for the two indicated mutations are shown.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

An "agonist" is a type of modulator and refers to an agent that binds a target and can activate one or more functions of the target. For example, an agonist of a protein can bind the protein and activate the protein in the absence of its natural or cognate ligand.

As used herein, an "antagonist" is a type of modulator and is used interchangeably with the term "inhibitor." In certain non-limiting embodiments, the term refers to an agent that binds a target (e.g., a protein) and can inhibit a one or more functions of the target. For example, an antagonist of an enzymatic protein can bind the protein and inhibit the enzymatic activity of the protein.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against TERT and used as TERT modulators.

As used herein, the term "effective," means adequate to accomplish a desired, expected, or intended result. More particularly, a "therapeutically effective amount" as provided herein refers to an amount of a TERT modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a TERT modulator, necessary to provide the desired therapeutic effect, e.g., an amount that is effective to prevent, alleviate, or ameliorate symptoms of disease or prolong the survival of the subject being treated. In a particular embodiment, the disease or condition is cancer. In a more specific embodiments, the cancer is thyroid cancer. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

The term "inhibitor" is a type of modulator and is used interchangeably with the term "antagonist." The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is TERT. The term also includes agents that have activity in addition to TERT inhibitory activity.

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "TERT modulator" refers to an agent that modulates the expressions and/or activity of TERT. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

Optional" or "optionally" means that the subsequently described event or circumstance can or cannot occur, and that the description includes instances where the event or circumstance occurs and instances where it does not.

The terms "patient," "individual," or "subject" are used interchangeably herein, and refer to a mammal, particularly, a human. The patient may have a mild, intermediate or severe disease or condition. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. In particular, the term also includes mammals diagnosed with a TERT mediated disease, disorder or condition. By "normal subject" is meant an individual who does not have cancer as well as an individual who has increased susceptibility for developing a cancer.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc., and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983).

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for TERT nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the TERT nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

The terms "sample," "patient sample," "biological sample," and the like, encompass a variety of sample types obtained from a patient, individual, or subject and can be used in a diagnostic or monitoring assay. The patient sample may be obtained from a healthy subject or a patient having symptoms associated with prostate cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cord blood, amniotic fluid, cerebrospinal fluid, urine, saliva, stool and synovial fluid), solid tissue samples such as a biopsy specimen or tissue cultures or cells derived therefrom and the progeny thereof. In certain embodiments, a sample comprises blood. In other embodiments, a sample comprises serum. In a specific embodiment, a sample comprises plasma. In yet another embodiment, a semen sample is used. In a further embodiment, a stool sample is used. In particular embodiments, TERT promoter mutations described here can be tested on tumor tissues, including surgical tissues, needle biopsy tissues (e.g., thyroid nodule needle biopsy specimens), body fluids (e.g., needle biopsy washings, cerebral spinal fluids, urine, etc.) for the diagnosis, prognosis and treatment guidance and treatments of cancer, such as thyroid cancer, bladder cancer, brain tumor/glioblastoma, and other cancers.

In certain embodiments, and in particular for the identification and treatment of bladder cancer, a sample comprises urine. Indeed, TERT mutations can be detected in urine as molecular markers for the diagnosis, prognostication and treatment of bladder cancer. See Hurst et al., 65 European Urology 367-69 (2014) ("Comprehensive Mutation Analysis of the TERT Promoter in Bladder Cancer and Detection of Mutations in Voided Urine"); and Rochakonda et al., 110 (43) Proc. Natl. Acad. Sci. USA 17426-17431 (October 2013) ("TERT Promoter Mutations in Bladder Cancer Affect Patient Survival and Disease Recurrence Through Modification by a Common Polymorphism").

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

By "specifically hybridizes" is meant that a probe, primer, or oligonucleotide recognizes and physically interacts (that is, base-pairs) with a substantially complementary nucleic acid (for example, a TERT nucleic acid) under high stringency conditions, and does not substantially base pair with other nucleic acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In a specific embodiment, the disease or condition is cancer including, but not limited to, thyroid, bladder and glioblastoma.

The terms "TERT-related disease, disorder or condition" or "TERT-mediated disease, disorder or condition," and the like mean diseases, disorders or conditions associated with aberrant TERT activity. In a specific embodiment, the disease or condition is cancer. In general, the term refers to any abnormal state that involves TERT activity. The abnormal state can be due, for example, to a genetic defect.

II. Tert Promoter Mutations as Biomarkers

The present inventors have discovered that certain mutations in the promoter region of TERT are associated with cancers including, but not limited to, thyroid cancer, bladder cancer and glioblastoma. Thyroid cancer can include follicular thyroid cancer (FTC), papillary thyroid cancer (PTC), conventional PTC, follicular variant PTC (FVPTC), tall-cell PTC (TCPTC).

Thus, in certain embodiments, the TERT promoter mutations can thus be used to identify individuals having or at risk of developing cancer. In further embodiments, the TERT promoter mutations can be used to identify individuals at risk for having or developing aggressive thyroid cancer such as TCPTC, PDTC, ATC, and BRAF-mutation-positive PTC. The mutations can be identified in subjects who have or have not been diagnosed with cancer.

In certain embodiments, DNA can be isolated from a biological sample taken from a subject. DNA can be extracted and purified from biological samples using any suitable technique. A number of techniques for DNA extraction and/or purification are known in the art, and several are commercially available (e.g., ChargeSwitch®, MELT™ total nucleic acid isolation system, MagMAX™ FFPE total nucleic acid isolation kit, MagMAX™ total nucleic acid isolation kit, QIAamp DNA kit, Omni-Pure™ genomic DNA purification system, WaterMaster™ DNA purification kit). Reagents such as DNAzol® and TR1 Reagent® can also be used to extract and/or purify DNA. DNA can be further purified using Proteinase K and/or RNAse.

In further embodiments, primer/probes can be used to amplify a region of the TERT gene that comprises the promoter. More specifically, primers/probes are capable of amplifying the promoter region at 1 295 228 C>T and 1 295 250 C>T (termed C228T and C250T respectively), corresponding to −124 C>T and −146 C>T from the translation start site in the promoter of the telomerase reverse transcriptase (TERT) gene. In one embodiment, a primer comprises the nucleic acid sequence shown in SEQ ID NO:2. In another embodiment, a primer comprises the nucleic acid sequence shown in SEQ ID NO:3. A primer set can comprise the nucleic acid sequences shown in SEQ ID NO:2 and SEQ ID NO:3.

In particular embodiments, a primer is contacted with isolated DNA from the subject under conditions such that the primer specifically hybridizes with the TERT gene. The primer and DNA thus form a primer:DNA complex. In certain embodiments, the hybridization conditions are such that the formation of the primer:DNA complex is the detection step itself, i.e., the complex forms only if the mutation (C228T and/or C250T) is present. In other embodiments, the primer:DNA complex is amplified using polymerase chain reaction, the presence (or not) of the mutation is detected. In certain embodiments, the mutations are detected by sequencing.

As described herein, in certain embodiments, the primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length in-between.

The probes or primers of the present invention can be prepared by conventional techniques well-known to those skilled in the art. For example, the probes can be prepared using solid-phase synthesis using commercially available equipment. Modified oligonucleotides can also be readily prepared by similar methods. The probes can also be synthesized directly on a solid support according to methods standard in the art. This method of synthesizing polynucleotides is particularly useful when the polynucleotide probes are part of a nucleic acid array.

The present invention therefore also provides predictive, diagnostic, and prognostic kits comprising degenerate primers to amplify a target nucleic acid in the TERT gene and instructions comprising amplification protocol and analysis of the results. The kit may alternatively also comprise buffers, enzymes, and containers for performing the amplification and analysis of the amplification products. The kit may also be a component of a screening, diagnostic or prognostic kit comprising other tools such as DNA microarrays. In some embodiments, the kit also provides one or more control templates, such as nucleic acids isolated from normal tissue sample, and/or a series of samples representing different variances in the TERT gene.

In one embodiment, the kit provides at least one primer capable of amplifying a different region of the TERT gene. The kit may comprise additional primers for the analysis of expression of several gene variances in a biological sample in one reaction or several parallel reactions. Primers in the kits may be labeled, for example fluorescently labeled, to facilitate detection of the amplification products and consequent analysis of the nucleic acid variances.

In one embodiment, more than one mutation/variance can be detected in one analysis. A combination kit will therefore comprise of primers capable of amplifying different segments of the TERT gene. A kit may also comprise primers capable of amplifying segments of another gene(s) including BRAF. The primers may be differentially labeled, for example, using different fluorescent labels, so as to differentiate between the variances. The primers contained within the kit may include primers selected from complementary sequences to the coding sequence of TERT.

In certain embodiments, a patient can be diagnosed or identified by adding a biological sample (e.g., blood or blood serum) obtained from the patient to the kit and detecting the TERT promoter mutations(s), for example, by a method which comprises the steps of: (i) collecting blood or blood serum from the patient; (ii) separating DNA from the patient's blood; (iii) adding the DNA from patient to a diagnostic kit; and, (iv) detecting (or not) the TERT promoter mutation(s). In this exemplary method, primers are brought into contact with the patient's DNA. The formation of the primer:DNA complex can, for example, be PCR amplified and, in some embodiments, sequenced to detect (or not) the TERT promoter mutation. In other kit and diagnostic embodiments, blood or blood serum need not be collected from the patient (i.e., it is already collected). Moreover, in other embodiments, the sample may comprise a tissue sample, urine or a clinical sample.

III. Tert Modulators

In certain embodiments, the TERT modulator is selected from the group consisting of a small molecule, a polypeptide, a nucleic acid molecule, a peptidomimetic, or a combination thereof. In a specific embodiment, the agent can be a polypeptide. The polypeptide can, for example, comprise an antibody. In another embodiment, the agent can be a nucleic acid molecule. The nucleic acid molecule can, for example, be a TERT inhibitory nucleic acid molecule. The TERT inhibitory nucleic acid molecule can comprise a short interfering RNA (siRNA) molecule, a microRNA (miRNA) molecule, or an antisense molecule.

A. Antibodies to TERT

The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

Various procedures known in the art may be used for the production of antibodies to TERT or any subunit thereof, or a fragment, derivative, homolog or analog of the protein. Antibodies of the present invention include, but are not limited to, synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

In some embodiments, an antibody specifically binds an epitope of the TERT protein. It is to be understood that the peptide regions may not necessarily precisely map one epitope, but may also contain a TERT sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., 157 J. MOL. BIOL. 105-32 (1982)); Hopp and Woods Analysis (Hopp, T. P. and Woods, K. R., 78 PROC. NATL. ACAD. SCI. USA 3824-28 (1981); Hopp, T. J. and Woods, K. R., 20 MOL. IMMUNOL. 483-89 (1983); Hopp, T. J., 88 J. IMMUNOL. METHODS 1-18 (1986)); Jameson-Wolf Analysis (Jameson, B. A. and Wolf, H., 4 COMPUT. APPL. BIOSCI. 181-86 (1988)); and Emini Analysis (Emini et al., 140 VIROLOGY 13-20 (1985)).

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the TERT antibodies that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identify contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half-life of an antibody, one may incorporate a salvage receptor binding epitope into the antibody (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-TERT antibodies of the present invention.

B. Small Molecule Modulators of TERT

In other embodiments, a TERT modulator is a small molecule. In a specific embodiment, the TERT modulator is the antagonist BIBR1532 (2-[(E)-3-naphthen-2-yl but-2-enoylamino]benzoic acid). See Ward & Autexier, Mol. Pharmacol. 68:779-786, 2005; also J. Biol. Chem. 277(18): 15566-72, 2002). TERT modulator antagonists can also include TMPyP4 (tetra-(N-methyl-4-pyridyl)porphyrin), telomerase inhibitor IX (MST312), MnTMPyp pentachloride, BPPA, β-Rubromycin, Trichostatin A, Costunolide, Doxorubicin, Suramin Sodium and (−)-Epigallocatchin Gallate (and other catechins). The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Compound libraries may be screened for TERT modulators. A compound library is a mixture or collection of one or more putative modulators generated or obtained in any manner. Any type of molecule that is capable of interacting, binding or has affinity for TERT may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative modulator or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to about 2000, 300 to about 3000, 300 to about 5000, 300 to about 6000, 300 to about 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation, A-Syntese-Biotech ApS, Akos-SC, G & J Research Chemicals Ltd., Life Chemicals, Interchim S.A., and Spectrum Info. Ltd.

C. RNA Interference Compositions for Targeting TERT mRNAs

In one aspect of the present invention, the expression of TERT may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al., 10 MOL. CELL. 549-61 (2002); Elbashir et al., 411 Nature 494-98 (2001)), micro-RNAs (miRNA)), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99(9) PROC. NATL. ACAD. SCI. USA, 6047-52 (2002); McManus et al., 8 RNA 842-50 (2002); Sui et al., 99(6) PROC. NATL. ACAD. SCI. USA 5515-20 (2002).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Highly Prevelant TERT Promoter Mutations in Aggressive Thyroid Cancers

Telomerase, a ribonucleoprotein complex that maintains telomere length at the end of chromosomes, plays a key role in cellular immortality and tumorigenesis (Smekalova et al. 2012, Mocellin et al. 2013). Its catalytic subunit is telomerase reverse transcriptase (TERT). Promoter mutations in the TERT gene on chromosome 5 have recently been reported in melanomas (Horn et al. 2013, Huang et al. 2013). Two TERT promoter mutations, 1295228 C>T and 1295250 C>T (termed C228T and C250T here respectively), are particularly common. They represent nucleotide changes of −124 C>T and −146 C>T (where −1 is the base just upstream of the A of the ATG translation start site) respectively in the TERT promoter. Both the mutations create an 11-base nucleotide stretch 5'-CCCCTTCCGGG-3' (SEQ ID NO:1), which contains a consensus binding site, GGAA (in reverse complement), for ETS transcription factors, suggesting potentially important biological relevance of these mutations. In fact, the two mutations have been demonstrated to confer increased transcriptional activity on the TERT promoter (Horn et al. 2013, Huang et al. 2013). These mutations are not found in normal human subjects and in the public genetic databases and are, therefore, cancer-specific somatic genetic alterations, further supporting their potentially important role in human tumorigenesis. This is consistent with the previously observed increased telomerase activities in some human cancers (Smekalova et al. 2012, Mocellin et al. 2013). Thus, TERT promoter mutations, by promoting the expression of the catalytic subunit of telomerase in response to ETS transcription factors, probably represent a novel mechanism by which telomerase plays an important role in human tumorigenesis. Melanomas and follicular cell-derived thyroid cancer share considerably similar genetic backgrounds; for example, they both harbor the BRAF V600E mutation with a high prevalence (Davies et al. 2002, Xing 2005a). We were, therefore, prompted to explore TERT promoter mutations in thyroid cancers in the present study.

Follicular cell-derived thyroid cancer is a common endocrine malignancy the incidence of which, similar to that of melanoma, has been rising rapidly globally in recent years (Jemal et al. 2011, Howlader et al. 2012). Follicular cell-derived thyroid cancer can be classified into several histological types (DeLellis et al. 2004), among which the most common types are papillary thyroid cancer (PTC) and follicular thyroid cancer (FTC), which account for 85-90% and 10-15% of all the thyroid cancers respectively (DeLellis et al. 2004, Jemal et al. 2011, Howlader et al. 2012). PTC can be further classified into a few subtypes or variants, the most common of which include conventional PTC (CPTC), follicular variant PTC (FVPTC), and tall-cell PTC (TCPTC). Other subtypes of PTC, such as the columnar variant, are rare. Unlike the rare but rapidly aggressive undifferentiated anaplastic thyroid cancer (ATC; Smallridge et al. 2012), PTC and FTC are indolent differentiated thyroid cancers (DTCs). There is also poorly differentiated thyroid cancer (PDTC), which has aggressiveness between that of DTC and ATC. Para-follicular C-cell-derived medullary thyroid cancer (MTC) is uncommon Benign thyroid tumors are far more common than thyroid cancers. Various genetic alterations have been identified in thyroid cancers, which, by aberrantly driving various signaling pathways, play a fundamental role in thyroid tumorigenesis (Xing 2013). In the present study, we examined TERT promoter mutations in various thyroid tumors to explore novel genetic alterations in thyroid tumorigenesis.

Materials and Methods

Thyroid Tumor Tissues, Cell Lines, and DNA. Genomic DNA was isolated from thyroid tumor tissues and cell lines using standard procedures of proteinase K digestion, phenol-chloroform extraction, and ethanol precipitation. Use of human thyroid tissues was based on Institutional Review Board-approved protocols and written patient consent was obtained where appropriate. The study included 85 benign thyroid tumors, 257 PTC (consisting of 187 CPTC, 56 FVPTC, 13 TCPTC, and 1 columnar PTC), 79 conventional FTC, 8 PDTC, 54 ATC, and 16 MTC samples. Thyroid cancer cell lines included TPC1, C643, Hth7, FTC133, OCUT-1, K1, FB1, BCPAP, SW1736, KAT18, Hth74, and WRO. Their thyroid tumor origins are given in Table 1.

TABLE 1

| TERT promoter mutation status of individual thyroid cancer cell lines | | | | | | | | | | | | |
|---|---|---|---|---|---|---|---|---|---|---|---|---|
| Cell lines | TPC1 | K1 | BCPAP | FTC133 | WRO | C643 | Hth7 | OCUT1 | SW1736 | KAT18 | Hth74 | FB1 |
| Tumor origin | PTC | PTC | PTC | FTC | FTC | ATC | ATC | ATC | ATC | ATC | ATC | ATC |
| TERT promoter mutation | C228T | C228T | CC229, 228TT | C228T | Wild-type | C228T | C250T | C250T | C228T | C228T | C250T | C228T |
| Zygosity | Heter | Heter | Heter | Homo | Homo | Heter | Homo | Homo | Heter | Heter | Homo | Heter |

Footnotes:
PTC, papillary thyroid cancer; FTC, follicular thyroid cancer; ATC, anaplastic thyroid cancer; "Heter", heterozygous; "Homo", homozygous.

Identification of TERT Promoter Mutations. Standard PCR was carried out for genetic sequencing to identify TERT promoter mutations. Briefly, a fragment of the TERT promoter was amplified by PCR on genomic DNA using primers 5'-AGTGGATTCGCGGGCACAGA-3' (SEQ ID NO:2) (sense) and 5'-CAGCGCTGCCTGAAACTC-3' (SEQ ID NO:3) (antisense). This resulted in a PCR product of 235 bp, containing the sites where mutations C228T and C250T occur in melanomas (Horn et al. 2013, Huang et al. 2013). About 40-50 ng of genomic DNA were used in the PCR, which was carried out with an initial denaturation step at 95° C. for 3 min, followed by ten cycles of 95° C. denaturation for 30 s, 55° C. annealing for 30 s, and 68° C. elongation for 1 min. This was then followed by 30 cycles of the same settings except for elongation for an additional 5 s in each cycle. The PCR was completed with a final elongation step at 68° C. for 7 min. Following quality confirmation of the PCR products by gel electrophoresis, sequencing PCR was carried out using a Big Dye terminator v3.1 cycle sequencing ready reaction kit (Applied Biosystems) and an ABI PRISM 3730 automated next generation genetic analyzer (Applied Biosystems) at the Johns Hopkins' sequencing facility. When a mutation was identified by Big Dye sequencing using the sense primer, the reaction was repeated using the antisense primer to confirm the mutation.

Identification of BRAF V600E Mutation. The BRAF V600E mutation was analyzed as described previously (Hu et al. 2006). Briefly, exon 15 of the BRAF gene containing the site for the T1799A (V600E) mutation was PCR-amplified using primers TCATAATGCTTGCTCTGATAGGA (SEQ ID NO:4) (sense) and GGCCAAAAATTTAATCA-GTGGA (SEQ ID NO:5) (antisense), resulting in a 212 bp product. The PCR settings included one cycle of 95° C. for 5 min; two cycles of 95° C. for 1 min, 60° C. for 1 min, and 72° C. for 1 min; two cycles of 95° C. for 1 min, 58° C. for 1 min, and 72° C. for 1 min; and 35 cycles of 95° C. for 1 min, 56° C. for 1 min, and 72° C. for 1 min, followed by an extension step at 72° C. for 5 min. After quality confirmation by agarose gel electrophoresis, the PCR products were subjected to Big Dye reaction and sequencing analysis as described above for TERT mutations. All the mutations were confirmed using both the sense and antisense primers.

Results

Example 1

Figure 1B:
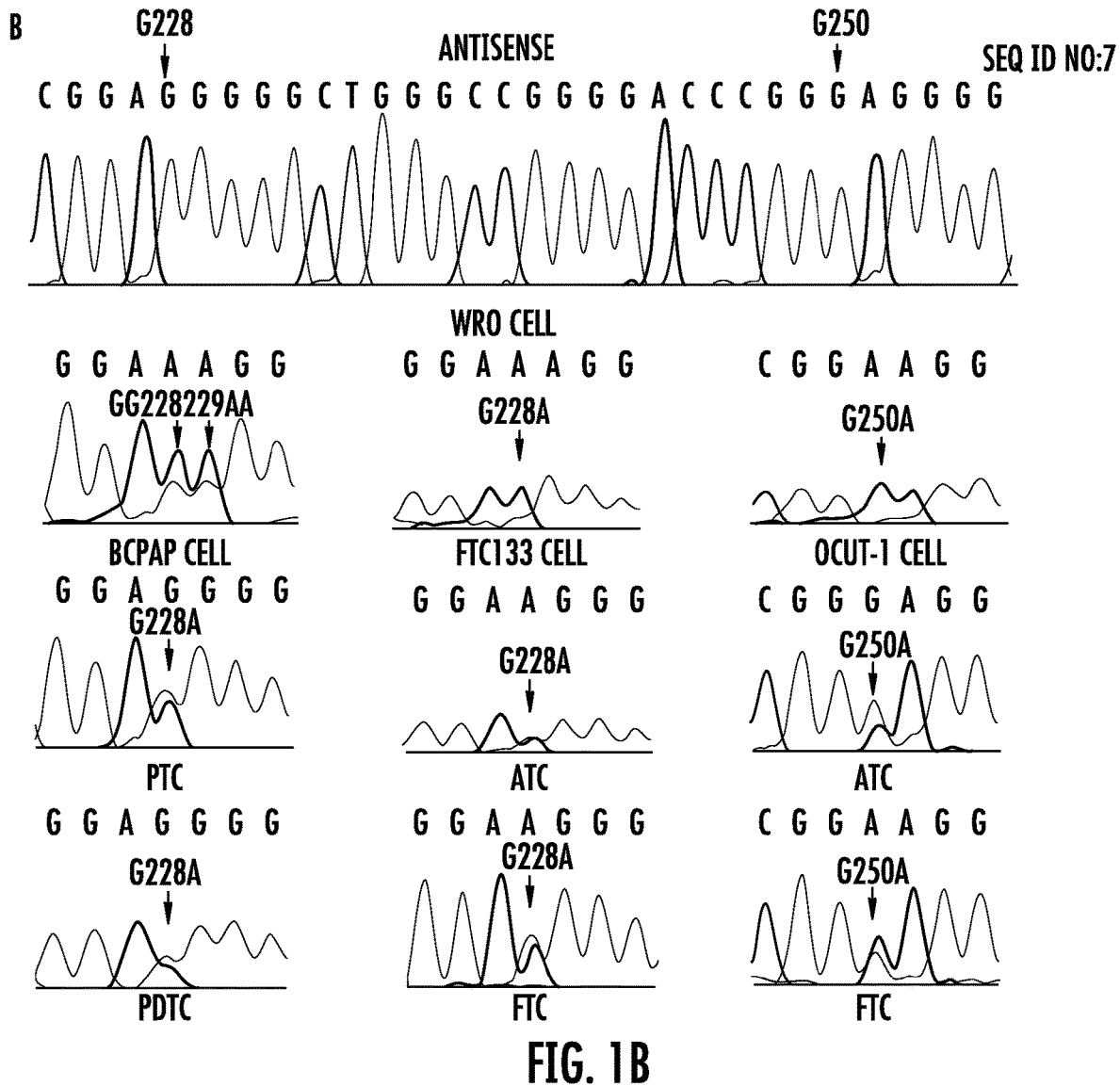

Prevalence of TERT Promoter Mutations in Thyroid Cancer Cell Lines and Thyroid Tumors In FIG. 1, representative electropherograms of the two TERT promoter mutations in thyroid cancer cell lines and various primary thyroid cancer tumor samples detected by both sense (FIG. 1A) and antisense (FIG. 1B) primers are shown. In Table 1, the TERT promoter mutation status of the 12 individual thyroid cancer cell lines tested is summarized. Except for the WRO cell line that harbored the wild-type TERT promoter, all the remaining 11 thyroid cancer cell lines examined harbored TERT promoter mutations. PTC and FTC cell lines only harbored the C228T mutation, while the ATC cell line harbored both the C228T and C250T mutations. Table 2 summarizes TERT promoter mutations found in all the thyroid cancer cell lines and primary thyroid tumors. The two mutations were collectively found in 11 of the 12 (91.7%) thyroid cancer cell lines. The C228T mutation was found in 0 of 85 (0.0%) benign thyroid tumor, 30 of 257 (11.7%) PTC, 9 of 79 (11.4%) FTC, 3 of 8 (37.5%) PDTC, and 23 of 54 (42.6%) ATC samples. Among the three variants of PTC, the C228T mutation was found in 4 of 13 (30.8%) TCPTC, 23 of 187 (12.3%) CPTC, and 2 of 56 (3.6%) FVPTC samples. The single columnar PTC sample examined was positive for the C228T mutation. The C250T mutation was not found in the PTC sample, but was found in two FTC, two ATC, and three ATC cell lines. The two TERT promoter mutations were mutually exclusive in both thyroid cancer cell lines and thyroid cancer tumor samples and collectively found in 11 of 79 (13.9%) FTC, 25 of 54 (46.3%) ATC, and 7 of 7 (100%) ATC cell lines. No TERT promoter mutation was found in 16 MTC samples. Three cases had both PTC and ATC in the same thyroid gland, and in each case, both the PTC and ATC harbored the C228T mutation. Three melanoma cell lines (M14, A375, and UACC62) examined harbored the C250T mutation (data not shown), as found in other melanoma cell lines (Horn et al. 2013, Huang et al. 2013). All the TERT mutations in the tumor samples were heterozygous, and some cell lines harbored a homozygous C228T or C250T mutation (Table 1). We also found a C>T mutation at position chromosome 5: 1295229, which is adjacent to the C228T mutation, resulting in a CC>TT tandem mutation in the BCPAP cell line (FIG. 1A). This is similar to the occasional finding of this tandem mutation in melanomas (Horn et al. 2013, Huang et al. 2013). A germline A>C (T>G on opposite strand) mutation at −57 bp from the ATG translation start site of the TERT gene was found in familial melanomas (Horn et al. 2013), but we did not find this mutation in any of the thyroid tumor samples or cell lines in the present study. We also did not find this mutation and other TERT promoter mutations in the peripheral blood DNA of 18 patients with familial PTC from a previous study (Xing 2005b).

TABLE 2

TERT promoter mutations in thyroid tumors

|  |  | Samples | Mutation C228T n/N (%) | Mutation C250T n/N (%) | Collective mutations n/N (%) |
|---|---|---|---|---|---|
| Thyroid cancer cell lines |  | PTC | 3/3 (100.0) | 0/3 (0.0) | 3/3 (100.0) |
|  |  | FTC | 1/2 (50.0) | 0/2 (0.0) | 1/2 (50.0) |
|  |  | ATC | 4/7 (57.1) | 3/7 (42.9) | 7/7 (100.0) |
|  |  | All | 8/12 (66.7) | 3/12 (25) | 11/12 (91.7) |
| Thyroid tumors |  | Benign tumor | 0/85 (0.0) | 0/85 (0) | 0/85 (0.0) |
|  | PTC | CPTC | 23/187 (12.3) | 0/187 (0.0) | 23/187 (12.3) |
|  |  | FVPTC | 2/56 (3.6) | 0/56 (0.0) | 2/56 (3.6) |
|  |  | TCPTC | 4/13 (30.8) | 0/13 (0.0) | 4/13 (30.8) |
|  |  | Columnar | 1/1 (100.0) | 0/1 (0.0) | 1/1 (100.0) |
|  |  | All | 30/257 (11.7) | 0/257 (0.0) | 30/257 (11.7) |
|  |  | FTC | 9/79 (11.4) | 2/79 (2.5) | 11/79 (13.9) |
|  |  | DTC | 39/336 (11.6) | 2/336 (0.6) | 41/336 (12.2) |
|  |  | PDTC | 3/8 (37.5) | 0/8 (0.0) | 3/8 (37.5) |
|  |  | ATC | 23/54 (42.6) | 2/54 (3.7) | 25/54 (46.3) |
|  |  | MTC | 0/16 (0.0) | 0/16 (0.0) | 0/16 (0.0) |

Footnotes:
PTC, papillary thyroid cancer;
CPTC, conventional PTC;
FVPTC, follicular variant PTC;
TCPTC, tall cell PTC;
FTC, follicular thyroid cancer;
DTC, differentiated thyroid cancer (combination of PTC and FTC);
PDTC, poorly differentiated thyroid cancer;
ATC, anaplastic thyroid cancer;
MTC, medullary thyroid cancer

Example 2

Association of TERT Promoter Mutations with Aggressive Types of Thyroid Cancers CPTC, FVPTC, and TCPTC account for the vast majority of PTC variants. TCPTC is classically known to be more aggressive than CPTC and FVPTC. As shown in Table 3, TERT promoter mutations were significantly more prevalent in the TCPTC samples than in the CPTC and FVPTC samples, 30.8% (4/13) in the former vs. 10.3% (25/243) in the latter two (P=0.046, per two-tailed Fisher's exact test). TERT promoter mutations were highly significantly more prevalent in the ATC samples than in the DTC samples, 46.3% (25/54) in the former vs. 12.2% (41/336) in the latter (P=$3 \times 10^{-8}$). There was a trend towards a higher prevalence of TERT promoter mutations in the PDTC samples than in the DTC samples, 37.5% (3/8) in the former vs. 12.2% (41/336) in the latter (P=0.069). Statistical significance was not reached, probably due to the relatively small number of PDTC samples.

TABLE 3

Association of TERT promoter mutations with aggressive thyroid cancers

| Types of thyroid cancer | Collective TERT promoter mutations, n/N (%) | P value* |
|---|---|---|
| TCPTC | 4/13 (30.8) | 0.046 |
| CPTC + FVPTC | 25/243 (10.3) | |
| ATC | 25/54 (46.3) | $3 \times 10^{-8}$ |
| DTC | 41/336 (12.2) | |
| PDTC | 3/8 (37.5) | 0.069 |
| DTC | 41/336 (12.2) | |

Footnotes:
PTC, papillary thyroid cancer;
TCPTC, tall-cell PTC;
CPTC, conventional PTC;
FVPTC, follicular variant PTC;
PDTC, poorly differentiated thyroid cancer;
DTC, differentiated thyroid cancer (combination of PTC and FTC);
ATC, anaplastic thyroid cancer.
*Per two-tailed Fisher's exact test.

Example 3

Association of TERT Promoter Mutation C228T with BRAF V600E Mutation in PTC

BRAF V600E mutation, which activates the MAPK pathway, is the most common mutation in thyroid cancers, particularly in PTC (Xing 2005a). We, therefore, analyzed the relationship between this mutation and TERT promoter mutation C228T in PTC. As shown in Table 4, TERT promoter mutation C228T more commonly occurred in the PTC samples harboring the BRAF V600E mutation than in the PTC samples harboring the wild-type BRAF gene, with a prevalence of 18.3% (19/104) in the former vs. 7.2% (11/153) in the latter (P=0.0094, per two-tailed Fisher's exact test). Conversely, BRAF mutation more commonly occurred in the PTC samples harboring the TERT promoter mutation than in the PTC samples harboring the wild-type TERT, 63.3% (19/30) in the former vs. 37.4% (85/227) in the latter (P=0.0094). Thus, the majority of the TERT promoter mutation-positive PTC samples harbored the BRAF V600E mutation. Several cases of ATC had both BRAF V600E and TERT mutations, but the relationship of the two types of mutations could not be statistically analyzed in this cancer due to the small number of BRAF mutation-positive cases (Table 4).

TABLE 4

Association of TERT promoter C228T mutation with the BRAF V600E mutation in papillary thyroid cancer

| Tumor type | TERT C228T mutation n/N (%) | | | BRAF V600E mutation n/N (%) | | |
|---|---|---|---|---|---|---|
|  | BRAF− | BRAF+ | P value* | TERT− | TERT+ | P value* |
| PTC | 11/153 (7.2) | 19/104 (18.3) | 0.0094 | 85/227 (37.4) | 19/30 (63.3) | 0.0094 |
| ATC | 20/44 (45.5) | 5/10 (50.0) | 1.0 | 5/29 (17.2) | 5/25 (20.0) | 1.0 |

Footnotes:
PTC, papillary thyroid cancer; ATC, anaplastic thyroid cancer.
*Per two-tailed Fisher's exact test.

DISCUSSION

The recent discovery of TERT promoter mutations in melanomas is the first example, to our knowledge, indicating that mutations in gene promoters may also play an important oncogenic role (Horn et al. 2013, Huang et al. 2013). This represents a novel genetic mechanism in human tumorigenesis. A subsequent report of the existence of TERT promoter mutations in other human cancers (Killela et al. 2013) and our report on the high prevalence of these mutations in bladder cancer and glioblastoma (Liu et al. 2013) suggest that TERT promoter mutations may play a huge role in human tumorigenesis. We report here for the first time, to our knowledge, that common TERT promoter mutations are also in observed thyroid cancer.

We found no TERT promoter mutations in para-follicular C-cell-derived MTC samples, consistent with similar findings in a recent study on 24 MTC samples (Killela et al. 2013). However, due to the relatively small number of samples examined, the status of TERT promoter mutations in MTC cannot be definitively concluded. In contrast, in the analysis of a large cohort of follicular cell-derived thyroid cancer samples in the present study, we found a common occurrence of TERT promoter mutations in both PTC and FTC samples, suggesting a role of these mutations in the tumorigenesis of a subgroup of these DTCs. The lack of TERT promoter mutations in benign thyroid tumor samples suggests that these mutations are malignancy-specific and may be relatively late genetic events along the line of thyroid tumorigenesis. Consistent with this idea is the strikingly higher prevalence of TERT promoter mutations in PDTC and ATC than in DTCs; PDTC and ATC have partially and completely lost differentiation respectively and are the most aggressive thyroid cancers. This raises the possibility that TERT promoter mutations may play a particular role in the de-differentiation of DTCs and hence their conversion to poorly or undifferentiated aggressive thyroid cancers. This possibility is consistent with the finding in three cases in which co-existing PTC and ATC in the same thyroid gland harbored TERT promoter mutation C228T. The prevalence of TERT promoter mutations was extremely high in thyroid cancer cell lines (91.7%), which is in contrast to the low prevalence of 16% (24/150) in general cancer cell lines from the Cancer Cell Line Encyclopedia (Huang et al. 2013), but is similar to the high prevalence of 74% (125/168) in melanoma cell lines (Horn et al. 2013). This result is again consistent with the idea that TERT promoter mutations may play a role in the de-differentiation of thyroid cancer cells since thyroid cancer cell lines in culture commonly become de-differentiated (van Staveren et al. 2007). Interestingly, among the three common variants of PTC, TCPTC harbored TERT promoter mutations with the highest prevalence. TCPTC is a relatively uncommon but more aggressive PTC variant than CPTC and FVPTC (Xing et al. 2005, Ghossein et al. 2007, LiVolsi 2010). It is possible that TERT promoter mutations play a role in the aggressiveness of this unique PTC variant. This is again consistent with the idea that TERT promoter mutations may play a role in the development of progression and aggressiveness of thyroid cancers.

As in many other human cancers in which telomerase activities are increased (Smekalova et al. 2012, Mocellin et al. 2013), increased telomerase activities have also been found in thyroid cancers but not in normal thyroid tissues or benign thyroid tumors, suggesting a role of this enzyme in thyroid cancer tumorigenesis (Capezzone et al. 2009). Both TERT promoter C228T and C250T mutations create binding sites for ETS transcription factors, which subsequently promote the expression of TERT (Horn et al. 2013, Huang et al. 2013). Thus, TERT promoter mutations may contribute to thyroid tumorigenesis by aberrantly promoting the expression of TERT. Interestingly, some ETS factors are targets of the MAPK signaling pathway (Janknecht et al. 1995, Whitmarsh et al. 1995, Strahl et al. 1996). The MAPK pathway aberrantly activated by BRAF V600E plays a fundamental role in the tumorigenesis and progression of PTC (Xing 2013). It is thus possible that TERT promoter mutations may join the mechanisms involving the MAPK signaling in thyroid tumorigenesis. Consistent with this hypothesis is the particularly high prevalence of TERT promoter mutations in BRAF V600E mutation-positive PTC and vice versa found in the present study. The preferential occurrence of TERT promoter mutations in BRAF V600E mutation-positive PTC is also consistent with the hypothesis discussed above that these TERT promoter mutations may play a role in the aggressiveness of thyroid cancers since BRAF V600E mutation-positive PTC is more aggressive than PTC with wild-type BRAF (Xing et al. 2005, 2013a). The association between TERT promoter and BRAF V600E mutations creates a unique mechanism for the amplification of TERT expression, in which TERT promoter mutations create binding sites for ETS transcription factors, which, upon activation by BRAF V600E-promoted MAPK signaling, initiate or augment the expression of TERT. Thus, the co-existence of TERT promoter and BRAF V600E mutations conceivably confers thyroid cancers with a unique survival advantage. New treatments targeting molecular targets, such as BRAF V600E, are being actively sought and tested for thyroid cancers (Xing et al. 2013b). The finding of TERT promoter mutations in thyroid cancers opens an exciting possibility for the development of novel therapeutic agents targeting TERT in thyroid cancer patients. Given the association of TERT promoter mutations with BRAF V600E mutation and their presumed interaction through enhancement of the function of ETS transcription factors in regulating the expression of TERT, this therapeutic strategy may be particularly effective in patients with both TERT promoter mutations and BRAF V600E mutation.

In summary, herein, we report for the first time, to our knowledge, common TERT promoter mutations in thyroid cancers, which are particularly prevalent in aggressive types of thyroid cancers and in BRAF V600E mutation-positive PTC. Their occurrence patterns in various types of thyroid cancers suggest that these TERT promoter mutations may play a role in the de-differentiation, progression, and aggressiveness of thyroid cancers. The discovery of this novel genetic background of thyroid cancers opens exciting new opportunities for biological and clinical research of thyroid cancers.

REFERENCES

1. Capezzone M, Marchisotta S, Cantara S & Pacini F 2009 Telomeres and thyroid cancer. Current Genomics 10 526-533.
2. Davies H, Bignell G R, Cox C, Stephens P, Edkins S, Clegg S, Teague J, Woffendin H, Garnett M J, Bottomley W et al. 2002 Mutations of the BRAF gene in human cancer. Nature 417 949-954.
3. DeLellis R A, Lloyd R, Heitz P U, Eng C (Eds) 2004 WHO Classification of Tumors, Pathology and Genetics-Tumors of Endocrine Organs. Lyon, France: IARC Press. Ghossein R A, Leboeuf R, Patel K N, Rivera M, Katabi N, Carlson D L, Tallini G, Shaha A, Singh B & Tuttle R M 2007 Tall cell variant of papillary thyroid carcinoma without extrathyroid extension: biologic behavior and clinical implications.
4. Horn S, Figl A, Rachakonda P S, Fischer C, Sucker A, Gast A, Kadel S, Moll I, Nagore E, Hemminki K et al. 2013 TERT promoter mutations in familial and sporadic melanoma. Science 339 959-961.
5. Howlader N, Noone A M, Krapcho M, Neyman N, Aminou R, Altekruse S F, Kosary C L, Ruhl J, Tatalovich Z, Cho H et al. (eds) 2012 SEER Cancer Statistics Review, 1975-2009 (Vintage 2009 Populations). Bethesda, Md.: National Cancer Institute (http://seer.cancer.gov/csr/1975_2009_pops09/, based on November 2011 SEER data submission, posted to the SEER web site, April 2012).
6. Hu S, Liu D, Tufano R P, Carson K A, Rosenbaum E, Cohen Y, Holt E H, Kiseljak-Vassiliades K, Rhoden K J, Tolaney S et al. 2006 Association of aberrant methylation of tumor suppressor genes with tumor aggressiveness and BRAF mutation in papillary thyroid cancer. International Journal of Cancer 119 2322-2329.
7. Huang F W, Hodis E, Xu M J, Kryukov G V, Chin L & Garraway L A 2013 Highly recurrent TERT promoter mutations in human melanoma. Science 339 957-959.
8. Janknecht R, Ernst W H & Nordheim A 1995 SAP1a is a nuclear target of signaling cascades involving ERKs. Oncogene 10 1209-1216.
9. Jemal A, Bray F, Center M M, Ferlay J, Ward E & Forman D 2011 Global cancer statistics. CA: A Cancer Journal for Clinicians 61 69-90.
10. Killela P J, Reitman Z J, Jiao Y, Bettegowda C, Agrawal N, Diaz L A Jr, Friedman A H, Friedman H, Gallia G L, Giovanella B C et al. 2013 TERT promoter mutations occur frequently in gliomas and a subset of tumors derived from cells with low rates of self-renewal. PNAS 110 6021-6026.
11. Liu X, Wu G, Shan Y, Hartmann C, von Deimling A & Xing M 2013 Highly prevalent TERT promoter mutations in bladder cancer and glioblastoma. Cell Cycle 12 1637-1638.
12. LiVolsi V A 2010 Papillary carcinoma tall cell variant (TCV): a review. Endocrine Pathology 21 12-15.
13. Mocellin S, Pooley K A & Nitti D 2013 Telomerase and the search for the end of cancer. Trends in Molecular Medicine 19 125-133.
14. Smallridge R C, Ain K B, Asa S L, Bible K C, Brierley J D, Burman K D, Kebebew E, Lee N Y, Nikiforov Y E, Rosenthal M S et al. 2012 American Thyroid Association 14. Anaplastic Thyroid Cancer Guidelines Taskforce. American Thyroid Association guidelines for management of patients with anaplastic thyroid cancer. Thyroid 22 1104-1139.

15. Smekalova E M, Shubernetskaya O S, Zvereva M I, Gromenko E V, Rubtsova M P & Dontsova O A 2012 Telomerase RNA biosynthesis and processing. Biochemistry 77 1120-1128.

16. van Staveren W C, Solis D W, Delys L, Duprez L, AndryG, Franc B, Thomas G, Libert F, Dumont J E, Detours V et al. 2007 Human thyroid tumor cell lines derived from different tumor types present a common dedifferentiated phenotype. Cancer Research 67 8113-8120.

17. Strahl T, Gille H & Shaw P E 1996 Selective response of ternary complex factor Sap1a to different mitogen-activated protein kinase subgroups. PNAS 93 11563-11568.

18. Whitmarsh A J, Shore P, Sharrocks A D & Davis R J 1995 Integration of MAP kinase signal transduction pathways at the serum response element. Science 269 403-407.

19. Xing M 2005a BRAF mutation in thyroid cancer. Endocrine-Related Cancer 12 245-262.

20. Xing M 2005b The T1799A BRAF mutation is not a germline mutation in familial nonmedullary thyroid cancer. Clinical Endocrinology 63 263-266.

21. Xing M 2013 Molecular pathogenesis and mechanisms of thyroid cancer. Nature Reviews. Cancer 13 184-199.

22. Xing M, Westra W H, Tufano R P, Cohen Y, Rosenbaum E, Rhoden K J, Carson K A, Vasko V, Larin A, Tallini G et al. 2005 BRAF mutation predicts a poorer clinical prognosis for papillary thyroid cancer. Journal of Clinical Endocrinology and Metabolism 90 6373-6379.

23. Xing M, Alzahrani A S, Carson K A, Viola D, Elisei R, Bendlova B, Yip L, Mian C, Vianello F, Tuttle R M et al. 2013a Association between BRAF V600E mutation and mortality in patients with papillary thyroid cancer. Journal of the American Medical Association 309 1493-1501.

24. Xing M, Haugen B R & Schlumberger M 2013b Promises in molecular-based management of differentiated thyroid cancer. Lancet 381 1058-1069.

Highly Prevalent TERT Promoter Mutations in Bladder Cancer and Glioblastoma

Telomerase reverse transcriptase (TERT) activities are frequently upregulated in human cancers, which is thought to be an important mechanism contributing to human tumorigenesis. Here, we investigated mutations in the TERT promoter—1,295,228 C>T and 1,295,250 C>T (termed C228T and C250T, respectively) in bladder cancer and glioblastoma. Use of primary bladder cancer and glioblastoma tissues was based on institutional review board-approved protocols. Genomic DNA from tumor tissues was isolated using standard procedures of protease K digestion, phenol-chloroform extraction and ethanol precipitation. A fragment of the TERT promoter was amplified by polymerase chain reaction (PCR) using primers 5'-AGTGGAT-TCGCGGGCACAGA-3' (SEQ ID NO:2) (sense) and 5'-CAGCGCTGCCTGAAACTC-3' (SEQ ID NO:3) (antisense), resulting in a PCR product of 235 bp, which contained the sites of C228T and C250T mutations. Amplification PCR was performed with an initial denaturation at 95° C. for 3 min, followed by 10 cycles of 95° C. denaturation for 30 sec, 55° C. annealing for 30 sec and 68° C. elongation for 1 min. This was followed by 30 cycles of the same settings except for the elongation for additional 5 sec in each cycle. Quality of PCR products was confirmed by gel electrophoresis. Sequencing PCR was performed using a Big Dye terminator v3.1 cycle sequencing ready reaction kit (Applied Biosystems) and an ABI PRISM 3730 automated next generation genetic analyzer (Applied Biosystems). Mutations were confirmed by repeating amplification PCR and using both primers in the Big Dye sequencing.

As summarized in Table 5, we found highly prevalent TERT promoter mutations in bladder cancer, bladder cancer cell lines and glioblastoma. C228T was far more common than C250T in all cases. Specifically, we found C228T in 81% (42/52) of bladder cancer samples and C250T in 4% (2/52) of samples. The two mutations were mutually exclusive in bladder cancer and were collectively found in 85% (44/52) of samples. C228T was found in 88% (⅞) of bladder cancer cell lines, and no C250T was found in these cell clines. We found C228T in 65% (48/74) of glioblastoma samples and C250T in 19% (14/74) of samples. The two mutations were also mutually exclusive in glioblastomas and were collectively found in 84% (62/74) of samples.

Our study on a large number of cases demonstrated a high prevalence of TERT promoter mutations in bladder cancer, establishing the common occurrence of these mutations in bladder cancer. This prevalence of 85% is unusually high for somatic mutations in any human cancer. We also found a high prevalence of TERT promoter mutations in glioblastoma, which like the prevalence of TERT promoter mutations in bladder cancer, is also unusually high for somatic mutations in any human cancer. Our finding of the high prevalence of TERT promoter mutations in bladder cancer and glioblastoma helps establish the common occurrence of this genetic alteration in the two cancers. Given the high prevalence, it is safe to assume that TERT promoter mutations play an important role in the tumorigenesis and pathogenesis of bladder cancer and glioblastoma.

Figure 2:
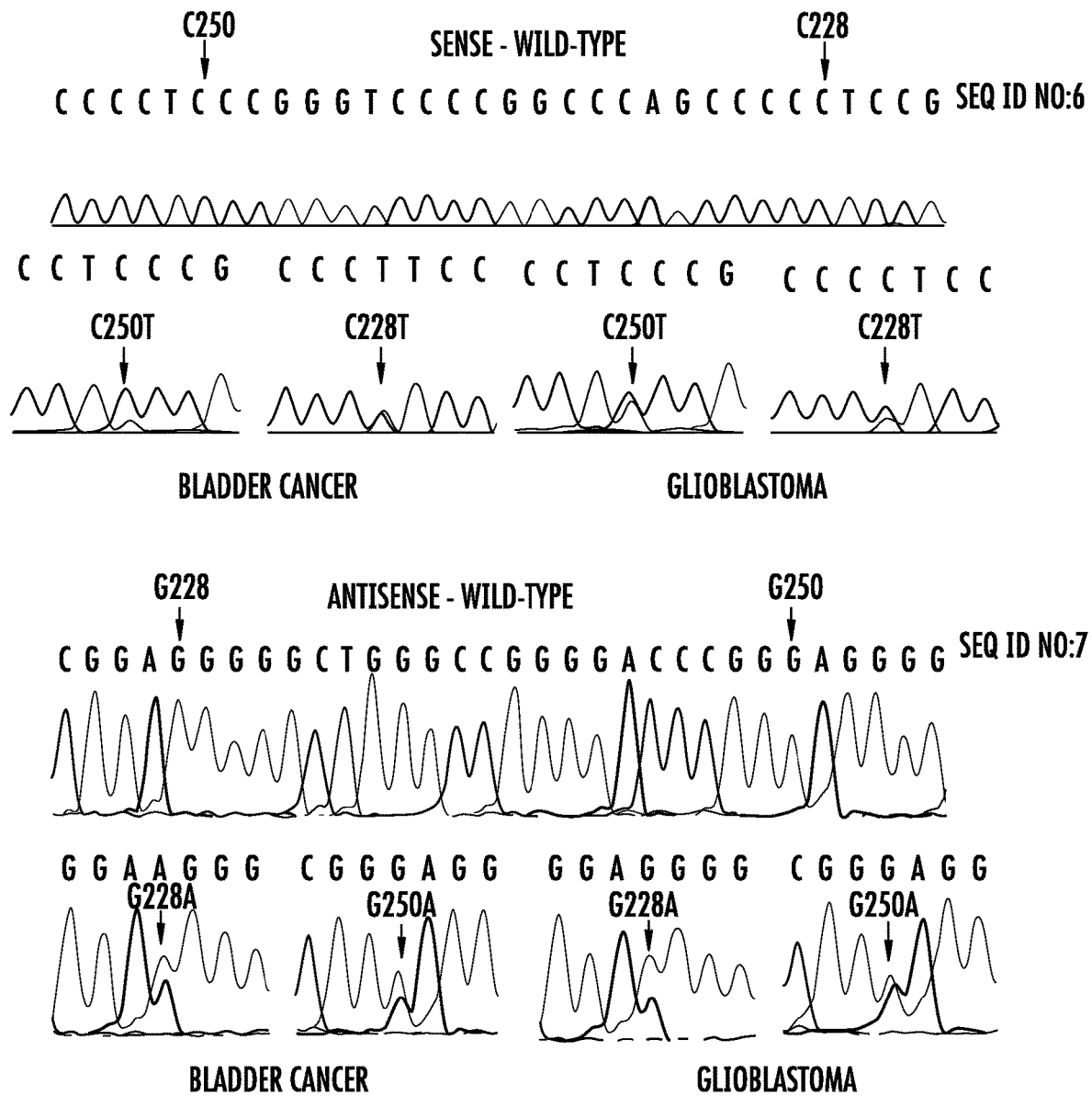
FIG. 2. TERT promoter mutations in bladder cancer and glioblastoma. Shown are representative electropherograms of the wild-type TERT promoter and two TERT promoter mutations as indicated for bladder cancer and glioblastoma. The upper portion of the figure shows electropherograms of the sense sequences of the wild-type DNA and the nucleotide changes of the two mutations in the two cancers. The lower portion of the figure shows the electropherograms of the antisense sequences of the wild-type DNA and the nucleotide changes of the two mutations in the two cancers.

With the high prevalence, testing of TERT promoter mutations for the diagnosis of bladder cancer and glioblastoma would be expected to have a high sensitivity. As these mutations are only found in cancers, testing of TERT promoter mutations are likely to be also highly specific for bladder cancer and glioblastoma. Both the C228T and C250T mutations create an 11-base nucleotide stretch 5'-CCCCTTCCGGG-3' (SEQ ID NO:1), which contains a consensus binding site, GGAA (in reverse complement), for ETS transcription factors. This has strong functional implications for these mutations; it is expected that these TERT promoter mutations would lead to upregulation of TERT through the action of ETS transcript factors in bladder cancer and glioblastoma. Indeed, the two mutations were demonstrated to confer upon the TERT promoter increased transcriptional activity. As such, these TERT mutations may be novel prognostic factors and therapeutic targets for bladder cancer and glioblastoma. Thus, the discovery of these TERT promoter mutations has strong clinical implications for the development of novel diagnostic, prognostic and therapeutic strategies for bladder cancer and glioblastoma as well as other cancers that may harbor these mutations (FIG. 2).

TABLE 5

TERT promoter mutations in bladder cancer and glioblastoma

| | TERT promoter mutations | | |
|---|---|---|---|
| Tumor types | 1,295,228 C > T (C228T) n/N (%) | 1,295,250 C > T (C250T) n/N (%) | Overall n/N (%) |
| Bladder cancer | 42/52 (80.77) | 2/52 (3.85) | 44/52 (84.62) |
| Bladder cancer cell lines | 7/8 (87.50) | 0/8 (0.00) | 7/8 (87.50) |
| Glioblastoma | 48/74 (64.86) | 14/74 (18.92) | 62/74 (83.78) |

REFERENCES

1. Smekalova et al., 77 BIOCHEMISTRY (MOSC.) 1120-28 (2012).
2. Mocellin et al., 19 TRENDS MOL. MED. 125-33 (2013).
3. Huang et al., 339 SCIENCE 957-59 (2013).
4. Horn et al., 339 SCIENCE 959-61 (2013).
5. Killela et al., 110 PROC. NATL. ACAD. SCI. USA 6021-26 (2013).

TERT Promoter Mutations in Other Cancers

As shown in Table 6, in addition to bladder cancer and brain tumors (glioblastoma), we found frequent TERT promoter mutations also in several other human cancers. Use of these mutations can also help develop novel diagnostic, prognostic and therapeutic strategies for these human cancers.

TABLE 6

TERT promoter mutations in human cancers

| | rs2853669 | TERT | 228 | 250 | 242 | NEW 273 |
|---|---|---|---|---|---|---|
| Bladder | 36/52 69.23% | 45/52 86.53% | 42/52 80.77% | 2/52 3.85% | 1/52 1.92% | |
| Brain tumors (Glioblastoma multiforme) | 22/47 46.81% | 36/47 76.6% | 31/47 65.96% | 5/47 10.64% | | |
| Breast | 42/76 55.26% | 4/76 5.26% | 1/76 1.32% | | | 3/76 3.95% |
| Colon | 7/25 28% | 0/25 0% | | | | |
| Ovarian Cancer | | 3/44 7% | | | | |

I claim:

1. A method for treating a subject having thyroid cancer comprising the steps of:
   (a) contacting DNA extracted from a biological sample obtained from the subject with at least one primer that specifically hybridizes to the telomerase reverse transcriptase (TERT) gene;
   (b) amplifying by polymerase chain reaction (PCR) a region of the TERT gene that comprises −124 and −146 from the translation start site in the promoter of the TERT gene;
   (c) sequencing the amplification product to detect the presence of a mutation at −124 (C228T) and/or −146 (C250T) from the translation start site in the promoter of the TERT gene; and
   (d) treating the subject having the C228T mutation and/or C250T mutation with one or more treatment modalities appropriate for a subject having thyroid cancer, wherein the treatment modalities comprise thyroidectomy, hemithyroidectomy, radioactive iodine therapy, and combinations thereof.

2. The method of claim 1, wherein the treatment modalities further comprise administering to the subject a TERT inhibitor, wherein the TERT inhibitor comprises BIBR1532, TMPyP4, MST312, MnTMPyp pentachloride, BPPA, β-Rubromycin, Trichostatin A, Costunolide, Doxorubicin, Suramin Sodium or (−)-Epigallocatechin Gallate.

3. A method for identifying a subject having thyroid cancer as likely to develop aggressive thyroid cancer comprising the steps of:
   (a) contacting DNA extracted from a biological sample obtained from the subject with at least one primer that specifically hybridizes to the TERT gene, where in the at least one primer comprises SEQ ID NO:2 and/or SEQ ID NO:3;
   (b) amplifying by PCR a region of the TERT gene that comprises −124 and −146 from the translation start site in the promoter of the TERT gene; and
   (c) sequencing the amplification product to detect the presence of a C228T mutation and/or a C250T mutation, wherein the detection of the mutation indicates the subject is likely to develop aggressive thyroid cancer.

4. The method of claim 3, further comprising the step of administering a treatment modality appropriate for a subject having or likely to develop aggressive thyroid cancer, wherein the treatment modality comprises thyroidectomy, hemithyroidectomy, radioactive iodine therapy, and combinations thereof.

5. The method of claim 4, wherein the treatment modality further comprises administering to the subject a TERT inhibitor, wherein the TERT inhibitor comprises BIBR1532, TMPyP4, MST312, MnTMPyp pentachloride, BPPA, β-Rubromycin, Trichostatin A, Costunolide, Doxorubicin, Suramin Sodium or (−)-Epigailocatechin Gallate.

6. The method of claim 1, wherein the at least one primer of step (a) comprises SEQ ID NO:2 and/or SEQ ID NO:3.

* * * * *